(12) United States Patent
Boileau et al.

(10) Patent No.: US 8,900,569 B2
(45) Date of Patent: *Dec. 2, 2014

(54) METHOD OF TREATING DIARRHEA IN A CANINE

(75) Inventors: Thomas William-Maxwell Boileau, Galloway, OH (US); Michael Anthony Ceddia, Newburg, IN (US); John Kevin Collins, Cork (IE); Gary Mitchell Davenport, Dayton, OH (US); Barry Pius Kiely, Cork (IE); Liam Diarmuid O'Mahony, Cork (IE); Gregory Dean Sunvold, Lewisburg, OH (US); Mark Alan Tetrick, Dayton, OH (US); Robert Jason Vickers, Dayton, OH (US)

(73) Assignees: The Iams Company, Mason, OH (US); Alimentary Health, County Cork (IE)

( * ) Notice: Subject to any disclaimer, the term of this patent is extended or adjusted under 35 U.S.C. 154(b) by 1043 days.

This patent is subject to a terminal disclaimer.

(21) Appl. No.: 12/148,313

(22) Filed: Apr. 18, 2008

(65) Prior Publication Data

US 2009/0010893 A1    Jan. 8, 2009

Related U.S. Application Data

(63) Continuation of application No. 11/012,946, filed on Dec. 15, 2004, now abandoned.

(60) Provisional application No. 60/531,588, filed on Dec. 19, 2003.

(51) Int. Cl.
| | | |
|---|---|---|
| *A01N 63/00* | (2006.01) | |
| *A23K 1/00* | (2006.01) | |
| *C12N 1/20* | (2006.01) | |
| *A23K 1/18* | (2006.01) | |
| *C12R 1/01* | (2006.01) | |
| *A23L 1/30* | (2006.01) | |
| *A61K 35/74* | (2006.01) | |

(52) U.S. Cl.
CPC . *C12R 1/01* (2013.01); *A23K 1/009* (2013.01); *A23K 1/008* (2013.01); *C12N 1/20* (2013.01); *A23K 1/1853* (2013.01); *A23K 1/1866* (2013.01); *A23K 1/1846* (2013.01); *A23K 1/186* (2013.01); *A23L 1/3014* (2013.01); *A61K 35/745* (2013.01)
USPC ...................................... 424/93.4; 435/252.1

(58) Field of Classification Search
None
See application file for complete search history.

(56) References Cited

U.S. PATENT DOCUMENTS

| | | |
|---|---|---|
| 2,540,979 A | 2/1951 | Clymer et al. |
| 3,320,130 A | 5/1967 | Henry |
| 3,431,338 A | 3/1969 | Munzel |
| 3,677,898 A | 7/1972 | Mitsugi et al. |
| 3,898,132 A | 8/1975 | Heltrick |
| 3,957,974 A | 5/1976 | Hata |
| 4,248,857 A | 2/1981 | DeNeale et al. |
| 4,314,995 A | 2/1982 | Hata et al. |
| 4,332,790 A | 6/1982 | Sozzi et al. |
| 4,338,346 A | 7/1982 | Brand |
| 4,399,163 A | 8/1983 | Brennan et al. |
| 4,411,925 A | 10/1983 | Brennan et al. |
| 4,423,029 A | 12/1983 | Rizzi |
| 4,434,231 A | 2/1984 | Jung |
| 4,518,696 A | 5/1985 | Gehrman et al. |
| 4,592,748 A | 6/1986 | Jost |
| 4,767,623 A | 8/1988 | Conway et al. |
| 4,781,939 A | 11/1988 | Martin et al. |
| 4,797,289 A | 1/1989 | Reddy |
| 4,806,368 A | 2/1989 | Reddy |
| 4,816,259 A | 3/1989 | Matthews et al. |
| 4,859,377 A | 8/1989 | Shasha et al. |
| 4,935,247 A | 6/1990 | Marttila et al. |
| 5,096,717 A | 3/1992 | Wirth et al. |
| 5,132,137 A | 7/1992 | Reimann et al. |
| 5,160,745 A | 11/1992 | DeLuca et al. |
| 5,171,580 A | 12/1992 | Iamartino et al. |
| 5,286,495 A | 2/1994 | Batich et al. |
| 5,322,686 A | 6/1994 | Grahn et al. |
| 5,413,960 A | 5/1995 | Dobrogosz et al. |
| 5,518,733 A | 5/1996 | Lamothe et al. |
| 5,531,988 A | 7/1996 | Paul |
| 5,540,945 A | 7/1996 | Ikushima |
| 5,569,634 A | 10/1996 | Miller et al. |
| 5,629,017 A | 5/1997 | Pozzi et al. |

(Continued)

FOREIGN PATENT DOCUMENTS

| | | |
|---|---|---|
| AU | 199928098 A1 | 7/1999 |
| CA | 1300538 | 5/1992 |

(Continued)

OTHER PUBLICATIONS

Apgar, G.A., et al., The Effect of Feeding Various Levels of *Bifidobacterium* globosum A on the Performance, Gastrointestinal Measurements, and Immunity of Weanling Pigs and on the Performance and Carcass Measurements of Growing-Finishing Pigs, J. Anim. Sci. (1993) vol. 71, pp. 2173-2179, 7 pages.

Biourge, Vincent, et al., The Use of Probiotics in the Diet of Dogs, The Journal of Nutrition (Dec. 1998) vol. 128 (12), pp. 2730S-2732S, France—Expanded Abstract, 3 pages.

Dunne, C., et al., Probiotics: from myth to reality. Demonstration of functionality in animal models of disease and in human clinical trials (1999) vol. 76, pp. 279-292, 14 pages.

(Continued)

*Primary Examiner* — Irene Marx

(74) *Attorney, Agent, or Firm* — Christopher D. Brandt; Tracey S. Truitt; William O. Adams

(57) ABSTRACT

According to the invention there is provided a strain of lactic acid bacteria of the species *Bifidobacteria globosum* obtainable by isolation from resected and washed canine gastrointestinal tract having a probiotic activity in animals. Methods of use and compositions comprising the *Bifidobacteria globosum* of the present invention are also provided.

7 Claims, 7 Drawing Sheets

(56) References Cited

U.S. PATENT DOCUMENTS

| | | | |
|---|---|---|---|
| 5,726,161 A | 3/1998 | Whistler | |
| 5,733,540 A | 3/1998 | Lee | |
| 5,766,520 A | 6/1998 | Bronshtein | |
| 5,785,990 A | 7/1998 | Langrehr | |
| 5,849,327 A | 12/1998 | Berliner et al. | |
| 5,853,697 A | 12/1998 | Strober et al. | |
| 5,910,447 A | 6/1999 | Lawrence et al. | |
| 5,976,579 A | 11/1999 | McLean | |
| 6,007,808 A | 12/1999 | DeHaen et al. | |
| 6,033,888 A | 3/2000 | Batich et al. | |
| 6,133,323 A | 10/2000 | Hayek | |
| 6,309,666 B1 | 10/2001 | Hatano et al. | |
| 6,310,090 B1 | 10/2001 | Hayek | |
| 2001/0018048 A1 | 8/2001 | Leer et al. | |
| 2001/0018071 A1 | 8/2001 | Cochran et al. | |
| 2002/0098235 A1 | 7/2002 | Dittmar et al. | |
| 2003/0157166 A1 | 8/2003 | Chen et al. | |
| 2003/0170217 A1 | 9/2003 | Collins et al. | |
| 2003/0190309 A1 | 10/2003 | Zink et al. | |
| 2004/0175389 A1 | 9/2004 | Porubcan | |
| 2005/0106133 A1 | 5/2005 | Zink et al. | |
| 2005/0152884 A1 | 7/2005 | Boileau et al. | |
| 2005/0158294 A1 | 7/2005 | Boileau et al. | |
| 2005/0175598 A1 | 8/2005 | Boileau et al. | |

FOREIGN PATENT DOCUMENTS

| | | |
|---|---|---|
| CA | 2256256 | 6/2000 |
| DE | 19819475 A1 | 4/1989 |
| DE | 19860375 A1 | 12/1998 |
| EP | 0168112 | 1/1986 |
| EP | 0212746 A2 | 3/1987 |
| EP | 0212747 A2 | 3/1987 |
| EP | 0298605 A1 | 11/1989 |
| EP | 0298605 B1 | 11/1989 |
| EP | 0366621 A1 | 2/1990 |
| EP | 0353581 A2 | 7/1990 |
| EP | 0391416 A1 | 10/1990 |
| EP | 0399819 A2 | 11/1990 |
| EP | 0439315 B1 | 7/1991 |
| EP | 0508701 B1 | 10/1992 |
| EP | 0627173 A1 | 7/1994 |
| EP | 0659769 A2 | 6/1995 |
| EP | 0659769 B1 | 6/1995 |
| EP | 0399819 B1 | 10/1995 |
| EP | 0850569 A1 | 1/1998 |
| EP | 0862863 B1 | 9/1998 |
| EP | 0956858 A1 | 11/1999 |
| EP | 0956858 B1 | 11/1999 |
| EP | 1010372 A2 | 6/2000 |
| EP | 0850569 B1 | 12/2000 |
| EP | 1312667 A1 | 5/2003 |
| FR | 2668081 A1 | 4/1992 |
| FR | 2615203 A1 | 11/1998 |
| GB | 1190387 | 5/1970 |
| GB | 1595054 | 8/1976 |
| GB | 1 503 094 A | 3/1978 |
| GB | 2241421 A | 4/1991 |
| GB | 2252228 A | 5/1992 |
| GB | 2245492 A | 8/1992 |
| GB | 2311027 A | 9/1997 |
| JP | 62201823 | 9/1987 |
| JP | 03076561 | 4/1991 |
| JP | 94256170 A | 9/1994 |
| JP | 96242763 A | 9/1996 |
| JP | 2000-191519 | 11/2000 |
| JP | 01278781 A | 10/2001 |
| RU | 2123343 C1 | 12/1998 |
| WO | WO 88/08452 A1 | 11/1988 |
| WO | WO 89/05849 A1 | 6/1989 |
| WO | WO 90/01335 A1 | 2/1990 |
| WO | WO 91/17672 A1 | 11/1991 |
| WO | WO 93/02558 A1 | 2/1993 |
| WO | WO 94/04180 A2 | 3/1994 |
| WO | WO 94/04180 A3 | 3/1994 |
| WO | WO 94/21284 A1 | 9/1994 |
| WO | WO 95/07090 A1 | 3/1995 |
| WO | WO 95/34292 A2 | 12/1995 |
| WO | WO 96/01612 A1 | 1/1996 |
| WO | WO 96/38159 A1 | 12/1996 |
| WO | WO 97/09448 A1 | 3/1997 |
| WO | WO 97/16198 A1 | 5/1997 |
| WO | WO 97/20577 A1 | 6/1997 |
| WO | WO 98/19968 A1 | 5/1998 |
| WO | WO 98/23727 A1 | 6/1998 |
| WO | WO 98/27967 A1 | 7/1998 |
| WO | WO 98/35014 A2 | 8/1998 |
| WO | WO 98/35014 A3 | 8/1998 |
| WO | WO 98/47374 A1 | 10/1998 |
| WO | WO 98/54982 A1 | 12/1998 |
| WO | WO 99/09839 A1 | 3/1999 |
| WO | WO 99/11245 A1 | 3/1999 |
| WO | WO 99/20745 A1 | 4/1999 |
| WO | WO 99/30576 A1 | 6/1999 |
| WO | WO 99/48372 A1 | 9/1999 |
| WO | WO 99/51108 A1 | 10/1999 |
| WO | WO 99/52511 A1 | 10/1999 |
| WO | WO 00/06127 A1 | 2/2000 |
| WO | WO 00/27364 A1 | 5/2000 |
| WO | WO 00/41707 A1 | 7/2000 |
| WO | WO 00/42168 A2 | 7/2000 |
| WO | WO 00/57712 A1 | 10/2000 |
| WO | WO 01/12164 A1 | 2/2001 |
| WO | WO 01/90311 A2 | 12/2001 |
| WO | WO 01/93011 A3 | 12/2001 |
| WO | WO 02/083879 A2 | 10/2002 |
| WO | WO 03/010297 A1 | 2/2003 |
| WO | WO 03/010298 A1 | 2/2003 |
| WO | WO 03/010299 A1 | 2/2003 |
| WO | WO 03/045356 A1 | 6/2003 |
| WO | WO 2005/060707 A | 7/2005 |
| WO | WO 2005/060708 A | 7/2005 |
| WO | WO 2005/060709 A | 7/2005 |
| WO | WO 2005/062879 A | 7/2005 |

OTHER PUBLICATIONS

Kaufmann, et al., Identification and Quantification of *Bifidobacterium* Species Isolated from Food with Genus-Specific 16S rRNA-Targeted Probes by Colony Hybridization and PCR, Applied and Environmental Microbiology (Apr. 1997) vol. 63 (4), pp. 1268-1273, 6 pages.

Leblond-Bourget, et al., 16S rRNA and 16S to 23S Internal Transcribed Spacer Sequence Analyses Reveal Inter- and Intraspecific *Bifidobacterium* phylogeny, Intl J. of System Bacteriology (Jan. 1996) vol. 46 (1), pp. 102-111, 10 pages.

Mattarelli, P., et al., Characterization of the Plasmid pVS809 From *Bifidobacterium* globosum, Microbiologica (1994) vol. 17, pp. 327-331, 5 pages.

Mentula, S., et al., Comparison between Cultured Small-Intestinal and Fecal Microbiotas in Beagle Dogs, Applied and Environmental Microbiology (Aug. 2005) vol. 71 (8), pp. 4169-4175, 7 pages.

Mitsuoka, T., et al., Ecology of the bifidobacteria, American J. of Clinical Nutrition (Nov. 1977) vol. 30, pp. 1799-1810, 12 pages.

Rinkinen, M., et al., Absence of host specificity for in vitro adhesion of probiotic lactic acid bacteria to intestinal mucus, Veterinary Microbiology (Dec. 2003) vol. 97 (1-2), pp. 55-56—Abstract, 1 page.

Simpson, P.J., et al., Genomic Diversity and Relatedness of Bifidobacteria Isolated from a Porcine Cecum, J. Bacteriology (Apr. 2003) vol. 185 (8), pp. 2571-2581, 11 pages.

Trovatelli, L.D., et al., Presence of Bifidobacteria in the Rumen of Calves Fed Different Rations, Applied and Environmental Microbiology (Oct. 1976) vol. 32 (4), pp. 470-473, 4 pages.

Yaeshima, et al., *Bifidobacterium* globosum, Subjective Synonym of *Bifidobacterium pseudolongum*, and Description of *Bifidobacterium pseudolongum* subsp. pseudolongum comb. nov. and *Bifidobacterium pseudolongum* subsp. globosum comb. nov., System Appl. Microbiol. (1992) vol. 15, pp. 380-385, 6 pages.

Zentek, J., et al., Dietary effects on bifidobacteria and *Clostridium perfringens* in the canine intestinal tract, J. Anim. Physiol. a. Anim. Nutr (Nov. 2003) vol. 87, pp. 397-407, Berlin, 12 pages.

(56) References Cited

OTHER PUBLICATIONS

EPO Search Report, mailed Apr. 2, 2009, 6 pages.
PCT Search Report, mailed Sep. 24, 2007, 7 pages.
Kyoto Yakuhin KK, "Sustains-Release Formulation Which Floats in Stomach—Comprises Core of Fats and Oils, Coated With Drug Containing Layer of e.g. Agar", *KYOT*, Oct. 7, 1987.
SS Pharmaceutical KK, Tablets Containing Double-Coated Granules—Obtained by Coating With Insol. Polymer, Enteric Polymer and/or Waxes, Then Further Coating With Water or Acid-Soluble Polymer, *SSSE*, Aug. 18, 1988.
Morishita Jintan KK, "Yogurt for Supply Physiologically Important Intestinal Bacteria—Contains Bacteria Contained in Capsule Having Inner Layer Made of Digestible Substance and Outer Layer Dissolving in Intestine", *MORI*, Mar. 10, 1995.
Lab Prod. Ethiques Ethypharm, "Coated Microgranules Containing a Gastric Protoon Pump Inhibitor With Two Hydrophobic Mateials, Free From Alkali and Any Ionic Surffactant", *Derwent Publications Ltd., Ethi*, May 21, 1999.
Freund Sangyokk, "Capsule Containing Useful Enteric Bacteria— Includes Hydrophobic Layer Non-Fluid at Room Temp Isolating Bacteria from Membrane, To Prevent Moisture Penetration", *Derwent Publication Ltd., FREN*, Aug. 5, 1986.
Morishita Jintan KK, "Capsule Preparation for Enteral Administration of Unsaturated Fatty Acids (Jpn)", *Derwent Publications Ltd., MORI*, Oct. 30, 1997.
Bodmeier R, "Capsule With Controlled Active Ingredient Release Comprises Active Ingredient-Containing Filling, Capsule Shell, Swelling Agent and Water-Insoluble Layer", *BODM*, May 18, 1999.
Snow Brand Milk Products, "Enteric Capsules—Comprising Core Containing Drug Etc. and Coating of Hardened Oil of M.Pt. Higher Than Body Temp. And Disintegrated by Lipase in Intestine", *Snow*, Mar. 31, 1986.
Takeda Chemical Ind KK, "Dry Coated Tablet—Comprises Core Tablets Containing Enzyme Prepn. In Enteric Films Within Outer Shell", *Take*, May 10, 1982.
Rogler et al., "Cytokines in Inflammatory Bowel Disease", *World Journal of Surgery*, vol. 22, 1998, pp. 382-389, XP002296948 the whole document.
O'Callaghan et al., "Human Cytokine Production by Mesenteric Lymph Node Cells in Response to Probiotic and Pathogenic Bacteria", *Gastroenterology*, vol. 122, No. 4 Suppl. 1, p. A-151 DDW Meeting Abstract Nr. S1040, Apr. 2002, XP009036734 the whole document.
Groux et al., "Regulatory T Cells and Inflammatory Bowel Disease", *Viewpoint Immunology Today*, Oct. 1999.
Gasche et al., "IL-10 Secretion and Sensitivity in Normal Human Intestine and Inflammatory Bowel Disease", *Journal of Clinical Immunology*, vol. 20, No. 5, 2000.
Hommes et al., "Anti- and Proinflammatory Cytokines in the Pathogenesis of Tissue Damage in Crohn's Disease", *2000 Lippincott Williams and Wilkins*, 1363-1950.
McKay et al., "Review article: In Vitro Models in Inflammatory Bowel Disease", *Aliment Pharmacol Ther*, 1997: 11 (Suppl. 3): 70-80.
L. Lakatos, "Immunology of Inflammatory Bowel Diseases", *Acta Physiologica Hungarica*, vol. 87 (4), pp. 355-372 (2000).
Powrie et al, "Inhibition of Th1 Responses Prevents Inflammatory Bowel Disease in Scid Mice Reconstituted with CD45Rbhi CD4+ T Cells"/, *Immunity*, vol. 1, 553-562, Oct. 1994.
Strober et al., "Reciprocal IFN-gamma and TGF-Beta Responses Regulate the Occurrence of Mucosal Inflammation", *Immunol Today*, Feb. 1997;18(2):61-4.
Chadwick et al."Activation of the Mucosal Immune System in Irritable Bowel Syndrome", *Gastroenterology*, (2002) 122:1778-83.
Anand et al."Cytokines and Inflammatory Bowel Disease", *Tropical Gastroenterology*, 1999; 20(3):97-106.
Favier et al., Fecal B-D-Galactosidase Production and Bifidobacteria are Decreased in Crohn's Disease, *Digestive Diseases and Sciences*, vol. 42, No. 4 (Apr. 1997), pp. 817-822.

Monteleone et al., "Manipulation of Cytokines in the Management of Patients With Inflammatory Bowel Disease", *Ann Med.*, Nov. 2000;32(8):552-60.
Rogler et al., "Cytokines in Inflammatory Bowel Disease", *World J Surg*, (1998) 22:382-9.
Henry J. Binder, M.D., "Genes, Bacteria and T Cells: Ingredients for Inflammatory Bowel Disease", Selected Summaries, *Gastroenterology*, 1998; 115: 1695-1600, vol. 115, No. 6.
Stallmach et al., "Induction and Modulation of Gastrointestinal Inflammation", *Trends Immunology Today*, Oct. 1998, vol. 19 No. 10 pp. 438-441.
Marteau et al., "Potential of Using Lactic Acid Bacteria for Therapy and Immunomodulation in Man", FEMS *Microbiology Reviews 12*, (1993) 207-220.
Vittorio Scardovi, "Irregular Nonsporing Gram-Positive Rods", *Genus Bifidobacterium* Orla-Jensen, 1924, 472.
Schmitt et al., "The Immunostimulatory Function of IL-12 in T-Helper Cell Development and Its Regulation by TGF-B, IFN-γ and IL-4", *Chem Immunet Basel Karger*, 1997, vol. 68, pp. 70-85.
Panwala et al., "A Novel Model of Inflammatory Bowel Disease: Mice Deficient for the Multiple Drug Resistance Gene, mdrla, Spontaneously Develop Colitis", *The American Association of Immunologists*, 1998, *The Journal of Immunology*, 1998 161: 5733-5744.
O'Mahony et al., "Probiotic Impact on Microbial Flora, Inflammation and Tumour Development in IL-10 Knockout Mice", *Aliment Pharmacol Ther*, 2001: 15: 1219-1225.
Medaglini et al., "Mucosal and Systemic Immune Responses to a Recombinant Protein Expressed on the Surface of the Oral Commensal Bacterium *Streptococcus gordonii* after oral colonization", *Proc. Natl. Acad. Sci. USA*, vol. 92, pp. 6868-6872, Jul. 1995 Medical Sciences.
Charteris et al., "Antiobiotic Sysceptibility of Potentially Probiotic *Bifidobacterium* Isolates From the Human Gastrointestinal Tract", *Letters in Applied Microbiology*, 1998, 26, 333-337.
McGee et al., "A Synergistic Relationship Between TNF-x, IL-1B, and TGF-B1 on IL-6 Secretion by the IEC-6 Intestinal Epithelial Cell Line", *Immunology*, 1995 86 6-11.
Bouhnik et al., "Effects of *Bifidobacterium* SP Fermented Milk Ingested With or Without Inulin on Colonic Bifidobacteria and Enezymatic activities in Healthy Humans" *European Journal of Clinical Nutrition*, (1996) 50, 269-273.
Charteris et al., "Development and application of an In Vitro Methodology to Determine the Transit Tolerance of Potentially Probiotic *Lactobacillus* and *Bifidobacterium* Species in the Upper Human Gastrointestinal Tract", *Journal of Applied Microbiology*, 1998, 84, 759-768—XP 000929203.
Charteris et al., "Antiobiotic Susceptibility of Potentially Probiotic *Bifidobacterium* Isolates from the Human Gastrointestinal Tract", *Letters of Applied Microbiology*, 1998, 26, 333-337.
Charteris et al., "Selective Detection, Enumeration and Identification of Potentially Probiotic *Lactobacillus* and *Bifidobacterium* Species in Mixed Bacterial Populations", *International Journal of Food Microbiology* 35, (1997) 1-27.
Chevalier et al., "Detection of *Bifidobacterium* Species by Enzymatic Methods", *Journal of Applied Basteriology*, 1990, 68, 619-624.
Collins et al., "Selection of Probiotic Strains for Human Applications", *In. Dairy Journal 8*, (1998) 487-490.
Gibson et al., "Dietary Modulation of the Human Gut Microflora Using Prebiotics", *Journal of Nutrition*,.(1998) 80. Suppl. 2 S209-S212.
Charteris et al., "Effect of Conjugated Bile Salts on Antibiotic Susceptibility of Bile Salt-Tolerant *Lactobacillus* and *Bifidobacterium* Isolates", *Journal of Food Protection*, vol. 63, No. 10, 2000, pp. 1369-1376.
Aranda et al., "Analysis of Intestinal Lymphocytes in Mouse Colitis Medicated by Transfer of CD4+, CD45RB high T Cells to SCID Recipients", 1997, *The American Association of Immunologists*.
Brandtzaeg et al., "Immunopathology of Human Inflammatory Bowel Disease", *Springer Seminars in Immunopathology*, (1997) 18: 555-589.
Chauviere et al., "Adhension of Human *Lactobacillus acidophilus* Strain LB to Human Enterocyte-like Caco-2 Cells", *Journal of General Microbiology*, (1992), 138, 1689-1696.

(56) References Cited

OTHER PUBLICATIONS

Cicco et al., "Inducible Production of Interleukin-6 by Human Polymorphonuclear Neutrophils: Role of Granulocyte-Macrophage Cology-Stimulating Factor and Tumor Necrosis Factor-Alpha", 1990 *The American Society of Hematology, Blood*, vol. 75, No. 10 May 15, 1990: pp. 2049-2052.

Donnelly et al., "Differential Regulation of Il-1 Production in Human Monocytes by IFN-y and IL-4", *The Journal of Immunology*, vol. 145, 569-575. No. 2 Jul. 15, 1990.

Iwasaki et al., "Unique Functions of CD11b+, CD8α+, and Double-Negative Peyer's Patch Dendritic Cells", 2001, *The American Association of Immunologists*.

Hildesheim et al., "Simultaneous Measurement of Several Cytokines Using Small Volumes of Biospecimens", *Cancer Epidemiology, Biomarkers & Prevention*, vol. IKI, pp. 1477-1484, Nov. 2002, XP002296946 abstract.

Andus et al., "Imbalance of the Interleukin 1 System in Colonic Mucosa—Association With Intestinal Inflammation and Interleukin 1 Receptor Agonist Genotype 2", *Gut*, vol. 41, 1997, pp. 651-657, p. 654, col. 2—p. 655, col. 1 figure 2D, XP002296947.

Van Damme et al., "The Proportion of Th1 Cells, Which Prevail in Gut Mucosa, Is Decreased in Inflammatory Bowel Syndrome", 2001, *Blackwell Science Ltd. Clinical and Experimental Immunology*, 125:383-390.

Hideo Tomomatsu, "Health Effrects of Oligosaccharides", 1994, *Food Technol*, 48, pp. 61-65.

Vickers et al., "Comparison of Fermentation of Selected Fructooligosaccharides and Other Fiber Substrates by Canine Colonic Microflora", *AJVR*, vol. 62, No. 4, Apr. 2001.

Wein et al., "Analyzing a Bioterror Attack on the Food Supply: The Case of Botolinum Toxin in Milk", 2005 by *The National Academy of Sciences of the USA*.

METHOD OF TREATING DIARRHEA IN A CANINE

CROSS REFERENCE TO RELATED APPLICATION

This application is a continuation of U.S. application Ser. No. 11/012,946, filed on Dec. 15, 2004, which claims the benefit of and priority to U.S. Provisional Application No. 60/531,588, filed on Dec. 19, 2003.

FIELD OF THE INVENTION

The present invention relates to the field of probiotic micro-organisms, more specifically canine probiotic lactic acid bacteria and methods of use.

BACKGROUND OF THE INVENTION

The defense mechanisms to protect the mammalian gastrointestinal (GI) tract from colonisation by pathogenic bacteria are highly complex. The GI tract of most mammals are colonised by native microflora, and invasive pathogenic micro-organisms. In a healthy individual, these competing microflora are in a state of equilibrium. Modification of the intestinal microflora equilibrium may lead to or prevent many GI disorders, both in humans, and other mammalian species, such as companion animals including cats, dogs and rabbits. The well being of companion animals is closely related to their feeding and GI health, and maintenance of the intestinal microflora equilibrium in these animals may result in healthier pets.

The number and composition of the intestinal microflora tend to be stable, although age and diet may modify it. Gastric acidity, bile, intestinal peristalsis and local immunity are factors thought to be important in the regulation of bacterial flora in the small intestine of human beings and various other mammals. Often pet GI disorders, including those found in canines and felines, are linked to bacterial overgrowth and the production of enterotoxins by pathogenic bacteria. These factors disrupt the intestinal microflora equilibrium and can promote inflammation and aberrant immune responses.

During the last few years, research has begun to highlight some valuable strains of bacteria and their potential use as probiotic agents. Probiotics are considered to be preparations of bacteria, either viable or dead, their constituents such as proteins or carbohydrates, or purified fractions of bacterial ferments that promote mammalian health by preserving and promoting the natural microflora in the GI tract, and reinforcing the normal controls on aberrant immune responses. It is believed by some that probiotic bacteria are more effective when derived from the species, or a closely related species to the individual intended to be treated. Therefore, there is a need for probiotic strains derived from companion animals to be used for companion animals, that are different to those derived from humans.

WO 01/90311 discloses probiotic micro-organisms isolated from faecal samples obtained from cats and dogs having probiotic activity. However, these bacteria were obtained from faecal samples, and may not form part of the natural intestinal microflora present in the upper portion of the GI tract.

Consequently, there is a need to provide strains of bacteria obtainable by isolation from the natural intestinal microflora present in the upper portion of the GI tract that are particularly adapted for companion animals, and have been selected for their probiotic properties and ability to survive processing, and to incorporate these strains into compositions that are suitable for their use.

SUMMARY OF THE INVENTION

According to the invention there is provided a strain of lactic acid bacteria of the species *Bifidobacterium globosum* obtainable by isolation from resected and washed canine gastrointestinal tract having a probiotic activity in animals.

In a preferred embodiment, the lactic acid bacterial strain is a *Bifidobacterium globosum* having a 16s-23s spacer region DNA sequence having at least 93% homology to SEQ. ID NO. 1.

In a further preferred embodiment, the lactic acid bacterial strain is *Bifidobacterium globosum* AHCF (NCIMB 41198).

Furthermore, the present invention is directed towards providing uses of *Bifidobacterium globosum* bacteria obtainable by isolation from resected and washed canine gastrointestinal tract for maintaining and improving pet health, and compositions comprising the lactic acid bacteria.

These and other features, aspects, and advantages of the present invention will become evident to those skilled in the art from a reading of the present disclosure.

DETAILED DESCRIPTION OF THE INVENTION

Figure 1:
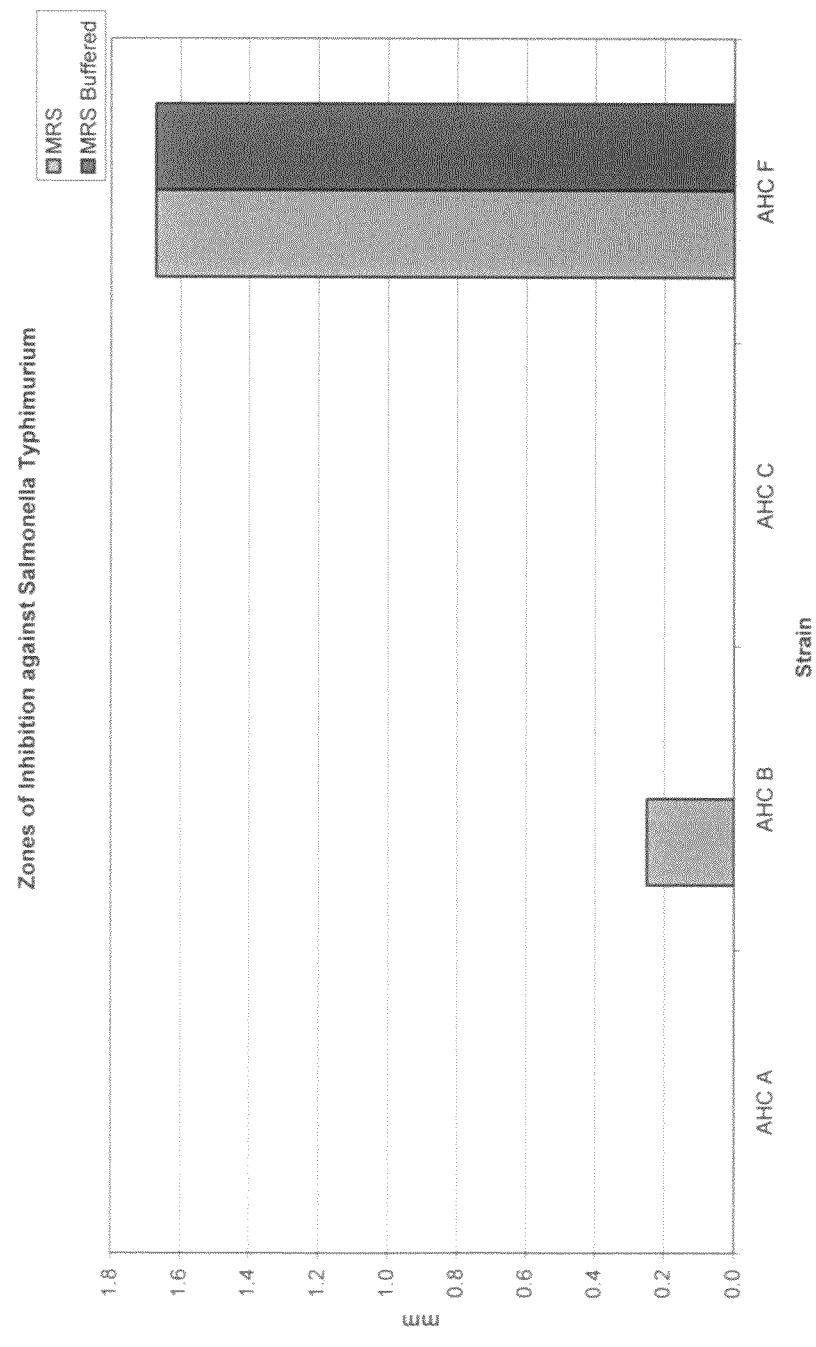
FIG. 1 demonstrates the inhibition of the growth in vitro of *Salmonella typhimurium* by the *Bifidobacterium globosum* bacteria of the present invention according to methodology set out in example 2.
Figure 2:
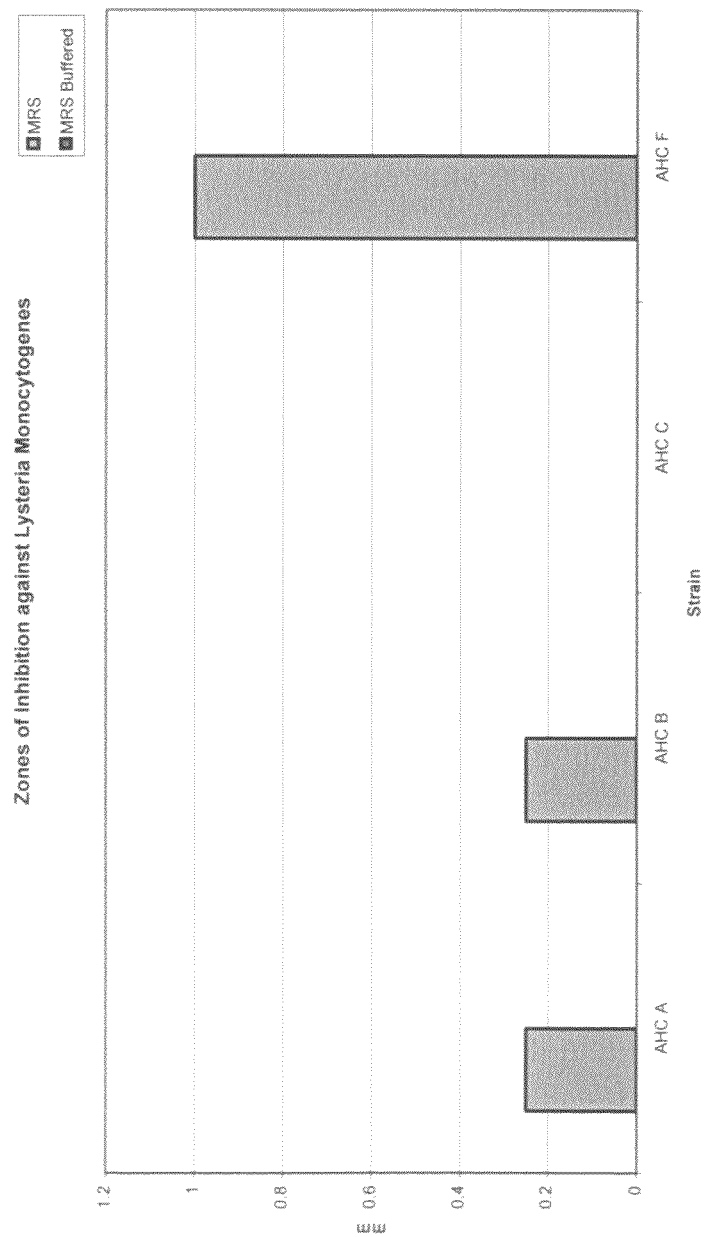
FIG. 2 demonstrates the inhibition of the growth in vitro of *Listeria monocytogenes* by the *Bifidobacterium globosum* bacteria of the present invention according to methodology set out in example 2.
Figure 3:
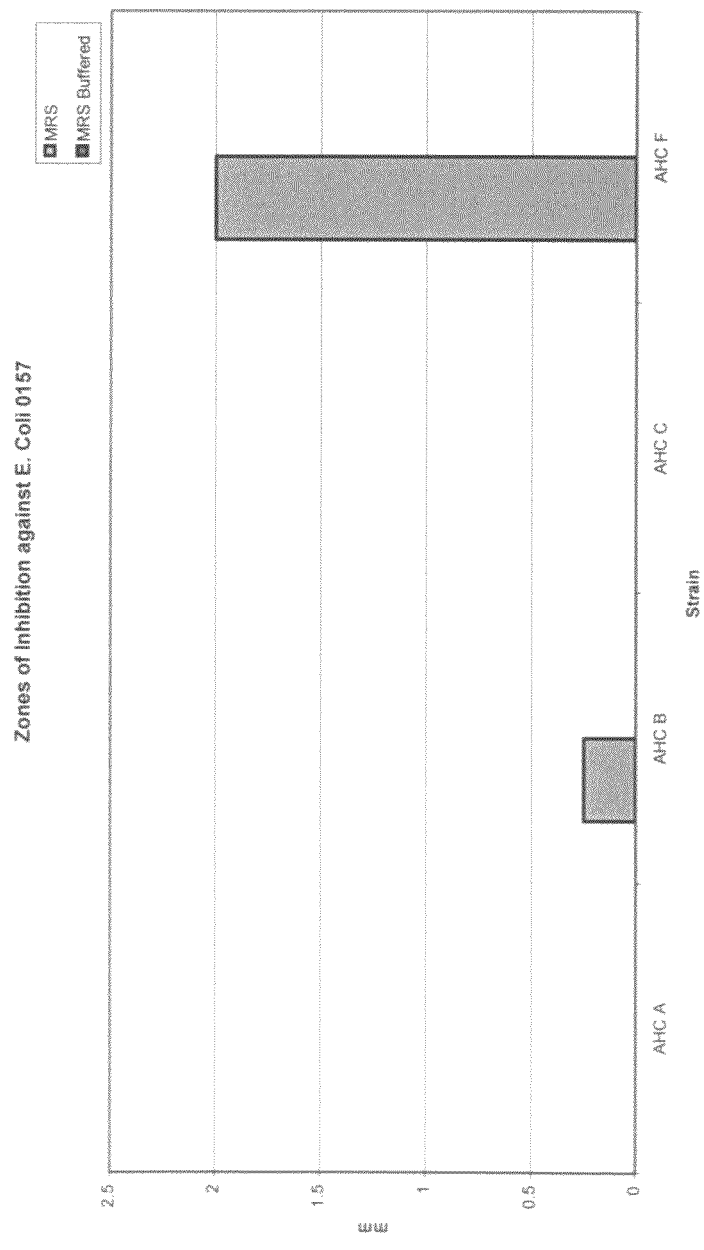
FIG. 3 demonstrates the inhibition of the growth in vitro of *Listeria innocua* by the *Bifidobacterium globosum* bacteria of the present invention according to methodology set out in example 2.
Figure 4:
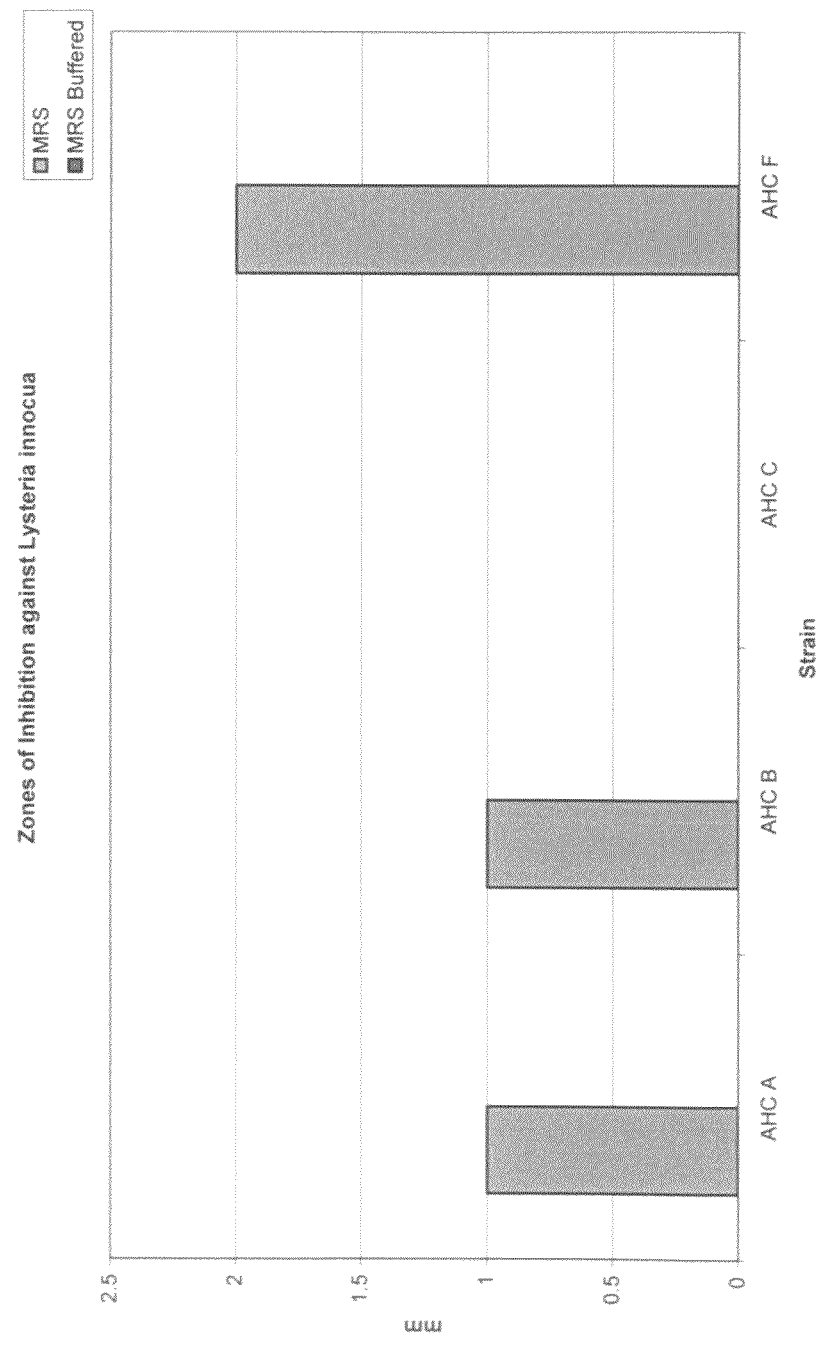
FIG. 4 demonstrates the inhibition of the growth in vitro of *Escherichia coli* 0157H45 by the *Bifidobacterium globosum* bacteria of the present invention according to methodology set out in example 2.

This application contains a sequence listing, described hereinafter, which is represented by a paper copy of the sequence listing attached to the amendment of Aug. 1, 2008, which is hereby incorporated by reference herein.

Sequences

SEQ. ID NO. 1—16s-23s intergenic spacer nucleotide sequence from *Bifidobacteria globosum* AHCF (NCIMB 41198).

SEQ. ID NO. 2—16s-23s left PCR primer sequence for sequence analysis.

SEQ. ID NO. 3—16s-23s right PCR primer sequence for sequence analysis.

Bacterial Deposit Numbers

The table below indicates *Bifidobacterium globosum* strain that are example of the present invention. The bacterial strain is deposited with the National Collections of Industrial Food and Marine Bacteria, Ltd. (NCIMB, Ltd.), Ferguson Building, Craibstone Estate, Bucksburn, Aberdeen AB21 9YA, Scotland UK, under deposit number NCIMB 41198, on Sep. 4, 2003.

| Strain | Deposit Number | 16s-23s Sequence |
|---|---|---|
| *Bifidobacterium globosum* AHCF | NCIMB 41198 | SEQ. ID NO. 1 |

All weights, measurements and concentrations herein are measured at 25° C. on the composition in its entirety, unless otherwise specified.

Unless otherwise indicated, all percentages of compositions referred to herein are weight percentages and all ratios are weight ratios.

Unless otherwise indicated, all molecular weights are weight average molecular weights.

Unless otherwise indicated, the content of all literature sources referred to within this text are incorporated herein in full by reference.

Except where specific examples of actual measured values are presented, numerical values referred to herein should be considered to be qualified by the word "about".

Within the following description, the abbreviation CFU ("colony-forming unit") designates the number of bacterial cells revealed by microbiological counts on agar plates, as will be commonly understood in the art.

As used herein, the term "mutants thereof" includes derived bacterial strains having at least 93% homology, preferably at least 96% homology, more preferably 98% homology to the 16s-23s intergenic spacer polynucleotide sequence of a referenced strain, but otherwise comprising DNA mutations in other DNA sequences in the bacterial genome.

As used herein, the term "DNA mutations" includes natural or induced mutations comprising at least single base alterations including deletions, insertions, transversions, and other DNA modifications known to those skilled in the art, including genetic modification introduced into a parent nucleotide or amino acid sequence whilst maintaining at least 50% homology to the parent sequence. Preferably, the sequence comprising the DNA mutation or mutations has at least 60%, more preferably at least 75%, more preferably still 85% homology with the parental sequence. As used herein, sequence "homology" can be determined using standard techniques known to those skilled in the art. For example, homology may be determined using the on-line homology algorithm "BLAST" program, publicly available at http://www.ncbi.nlm.nih.gov/BLAST/.

As used herein "genetic modification" includes the introduction of exogenous and/or endogenous DNA sequences into the genome of an organism either by insertion into the genome of said organism or by vectors including plasmid DNA or bacteriophage as known by one skilled in the art, said DNA sequence being at least two deoxyribonucleic acid bases in length.

As used herein, "companion animal" means a domestic animal. Preferably, "companion animal" means a domestic canine, feline, rabbit, ferret, horse, cow, or the like. More preferably, "companion animal" means a domestic canine or feline.

*Bifidobacteria globosum* Strains

The first aspect of the present invention comprises a strain of *Bifidobacterium globosum* obtainable by isolation from resected and washed canine gastrointestinal tract having probiotic activity in animals. Probiotics are micro-organisms, either viable or dead, processed compositions of micro-organisms, their constituents such as proteins or carbohydrates, or purified fractions of bacterial ferments that beneficially affect a host. The general use of probiotic bacteria is in the form of viable cells. However, it can be extended to non-viable cells such as killed cultures or compositions containing beneficial factors expressed by the probiotic bacteria. This may include thermally killed micro-organisms, or micro-organisms killed by exposure to altered pH or subjected to pressure. For the purpose of the present invention, "probiotics" is further intended to include the metabolites generated by the micro-organisms of the present invention during fermentation, if they are not separately indicated. These metabolites may be released to the medium of fermentation, or they may be stored within the micro-organism. As used herein "probiotic" also includes bacteria, bacterial homogenates, bacterial proteins, bacterial extracts, bacterial ferment supernatants, and mixtures thereof, which perform beneficial functions to the host animal when given at a therapeutic dose.

It has been found that strains of *Bifidobacterium globosum* obtainable by isolation directly from resected and washed GI tract of mammals are adherent to the GI tract following feeding of viable bacterial cells, and are also significantly immunomodulatory when fed to animals in viable, non-viable or fractionated form. Without being bound by theory, it is believed that the *Bifidobacterium globosum* obtainable by isolation from resected and washed GI tract closely associate with the gut mucosal tissues. Without further being bound by theory, this is believed to result in the probiotic *Bifidobacterium globosum* of the present invention generating alternative host responses that result in its probiotic action. It has been found that probiotic bacteria obtainable by isolation from resected and washed GI tract can modulate the host's immune system via direct interaction with the mucosal epithelium, and the host's immune cells. This immunomodulation, in conjunction with the traditional mechanism of action associated with probiotic bacteria, i.e. the prevention of pathogen adherence to the gut by occlusion and competition for nutrients, results in the *Bifidobacterium globosum* of the present invention being highly efficacious as a probiotic organism.

The *Bifidobacterium globosum* of the present invention, obtainable by isolation from resected and washed canine GI tract, have in vitro anti-microbial activity against a number of pathogenic bacterial strains/species, as measured by zones of inhibition or bacterial growth inhibition assays known to those skilled in the art. Without being bound by theory, it is believed that this in vitro anti-microbial activity is indicative of potential probiotic activity in vivo in animals, preferably companion animals such as canines and felines. The lactic acid bacteria of the present invention preferably have in vitro anti-microbial activity against *Salmonella typhimurium, Listeria monocytogenes, Listeria innocua* or *Escherichia coli*, more preferably a mixture of these strains, more preferably still, all of these strains.

Without being bound by theory, it is believed that the anti-microbial activity of the *Bifidobacterium globosum* bacteria of the present invention may be the result of a number of different actions by the *Bifidobacterium globosum* bacteria herein. It has previously been suggested in the art that several strains of bacteria isolated from faecal samples exert their probiotic effect in the GI tract following oral consumption by preventing the attachment of pathogenic organisms to the gut mucosa by occlusion. This requires oral consumption of "live" or viable bacterial cells in order for a colony of bacteria to be established in the gut. However, it is believed that the *Bifidobacterium globosum* of the present invention, obtainable by isolation from resected and washed canine GI tract, whilst exerting some probiotic effect due to occlusion if given in a viable form, may deliver a substantial probiotic effect in either the viable or non-viable form due to the production during fermentation in vitro of a substance or substances that either inhibit the growth of or kill pathogenic micro-organisms, and/or alter the host animal's immune competence. This form of probiotic activity is desirable, as the bacteria of the present invention can be given as either viable or non-viable cultures or purified fermentation products and still deliver a beneficial therapeutic effect to the host animal.

Preferably, the *Bifidobacterium globosum* bacteria of the present invention are able to maintain viability following transit through the GI tract. This is desirable in order for live cultures of the bacteria to be taken orally, and for colonization to occur in the intestines and bowel following transit through the oesophagus and stomach. Colonisation of the intestine and bowel by the lactic acid bacteria of the present invention is desirable for long-term probiotic benefits to be delivered to the host. Oral dosing of non-viable cells or purified isolates thereof induces temporary benefits, but as the bacteria are not viable, they are not able to grow, and continuously deliver a probiotic effect in situ. As a result this may require the host to be dosed regularly in order to maintain the health benefits. In contrast, viable cells that are able to survive gastric transit in the viable form, and subsequently colonise by adhering to and proliferating on the gut mucosa are able to deliver probiotic effects continuously in situ.

Therefore, it is preferable that the lactic acid bacteria of the present invention maintain viability after suspension in a media having a pH of 2.5 for 1 hour. As used herein, "maintain viability" means that at least 25% of the bacteria initially suspended in the test media are viable using the plate count method known to those skilled in the art. Preferably, "maintain viability" means that at least 50% of the bacteria initially suspended are viable. It is desirable for the lactic acid bacteria of the present invention to maintain viability following exposure to low pH as this mimics the exposure to gastric juices in the stomach and upper intestine in vivo following oral consumption in animals.

Furthermore, it is preferable that the lactic acid bacteria of the present invention have a growth of at least 33% when in the presence of at least 0.5% porcine bile salts. Growth, as used herein is described in further detail in example 3. More preferably, the bacteria of the present invention have a growth of at least 33% when in the presence of at least 1% porcine bile salts. Without being bound by theory it is believed that the lactic acid bacteria of the present invention, capable of growth in the presence of at least 0.5% porcine bile salts, are able to survive the conditions present in the intestine. This is thought to be a result of the addition of porcine bile to the culture medium mimicking the conditions of the intestine.

Further still, it is preferable that the *Bifidobacterium globosum* bacteria of the present invention have significant adhesion to gut epithelial cells in vitro. As used herein, "significant adhesion" means at least 4% of the total number of lactic acid bacteria co-incubated with the epithelial cells in vitro adhere to the epithelial cells. More preferably, at least 6% of bacterial cells co-incubated adhere to epithelial cells in vitro. Without being bound by theory, it is believed that gut epithelial cell adherence in vitro is indicative of the lactic acid bacteria's ability to colonise the GI tract of an animal in vivo.

The 16s-23s intergenic polynucleotide sequence is known to those skilled in the art as the sequence of DNA in the bacterial genome that can be used in order to identify different species and strains of bacteria. This intergenic polynucleotide sequence can be determined by the method detailed below in example 4.

In a preferred embodiment of the present invention, the strain of *Bifidobacterium globosum* has a 16s-23s intergenic polynucleotide sequence that has at least 93%, preferably at least 96%, more preferably at least 99% homology with the polynucleotide sequence according to SEQ. ID NO. 1. More preferably, the strain of lactic acid bacteria according to the present invention has a 16s-23s polynucleotide sequence according to SEQ. ID NO. 1. More preferably still, the strain of lactic acid bacteria according to the present invention is *Bifidobacterium globosum* strain NCIMB 41198 (AHCF), or a mutant thereof.

The strain of lactic acid bacteria of the genus *Bifidobacterium globosum* obtainable by isolation from resected and washed canine gastrointestinal tract can be used to deliver probiotic benefit following oral consumption in animals, preferably companion animals or humans. This probiotic benefit generally maintains and improves the overall health of the animal. Non-limiting elements of animal health and physiology that benefit, either in therapeutically relieving the symptoms of, or disease prevention by prophylaxis include inflammatory disorders, immunodeficiency, inflammatory bowel disease, irritable bowel syndrome, cancer (particularly those of the gastrointestinal and immune systems), diarrhoeal disease, antibiotic associated diarrhoea, appendicitis, autoimmune disorders, multiple sclerosis, Alzheimer's disease, amyloidosis, rheumatoid arthritis, arthritis, joint mobility, diabetes mellitus, insulin resistance, bacterial infections, viral infections, fungal infections, periodontal disease, urogenital disease, surgical associated trauma, surgical-induced metastatic disease, sepsis, weight loss, weight gain, excessive adipose tissue accumulation, anorexia, fever control, cachexia, wound healing, ulcers, gut barrier infection, allergy, asthma, respiratory disorders, circulatory disorders, coronary heart disease, anaemia, disorders of the blood coagulation system, renal disease, disorders of the central nervous system, hepatic disease, ischaemia, nutritional disorders, osteoporosis, endocrine disorders, and epidermal disorders. Preferred are treatment of the gastrointestinal tract, including treatment or prevention of diarrhoea; immune system regulation, preferably the treatment or prevention of autoimmune disease and inflammation; maintaining or improving the health of the skin and/or coat system, preferably treating or preventing atopic disease of the skin; ameliorating or reducing the effects of aging, including mental awareness and activity levels; and preventing weight loss during and following infection.

The treatment of the disorders disclosed above may be measured using techniques known to those skilled in the art. For example, inflammatory disorders including autoimmune disease and inflammation may be detected and monitored using in vivo immune function tests such as lymphocyte blastogenesis, natural killer cell activity, antibody response to vaccines, delayed-type hypersensitivity, and mixtures thereof. Such methods are briefly described herein, but well known to those skilled in the art.

1. Lymphocyte blastogenesis: This assay measures the proliferative response in vitro of lymphocytes isolated from fresh whole blood of test and control animals to various mitogens and is a measure of overall T- and B-cell function. Briefly, peripheral blood mononucleocytes (PBMC) are isolated from whole blood by Ficoll-Hypaque density centrifugation methods known to those skilled in the art. The isolated PBMCs are washed twice in RPMI 1640 cell media supplemented with HEPES, L-glutamine and penicillin/streptomycin. The washed cells are resuspended in RPMI 1640, counted, and the cell density adjusted appropriately. The $2\times10^5$ cells are exposed to a range of concentrations (0.1 □ g/ml to 100 □ g/ml) of various mitogens, some examples of which include pokeweed mitogen (Gibco), phytohaemaggluti-nin (Gibco) and conconavalin A (Sigma) in triplicate for 72 hours at 37° C. and 5% $CO_2$ with 10% foetal bovine serum (Sigma). At 54 hours the cells are pulsed with 1 □ Ci $^3$H-thymidine, and the cells harvested and scintilla-tion counts read on a TopCount NXT at 72 hours.

2. Natural killer cell activity: As described in U.S. Pat. No. 6,310,090, this assay measures the in vitro effector activity of natural killer cells isolated from fresh whole blood of test and control animals. Natural killer cells are a component of the innate immune function of a mam-mal. Canine thyroid adenocarcinoma cells were used as target cells in assessing NK cell cytotoxic activity. This cell line was previously shown to be susceptible to kill-ing by canine NK cell. Target cells were cultured in a T75 flask with 20 mL minimum essential medium (MEM; Sigma Chem. Co., St. Louis, Mo.) supple-mented with 10% fetal calf serum (FCS), 100 U/mL of penicillin and 100 □ g/mL of streptomycin. When con-fluent, target cells were trypsinized, washed 3 times and resuspended to $5\times10^5$ cells/mL in complete medium (RPMI-1640+10% FCS+100 U/mL of penicillin+100 □ g/mL of streptomycin). Triplicate 100.□ L aliquots of the target cells were pipetted into 96-well U-bottom plates (Costar, Cambridge, Mass.) and incubated for 8 hours to allow cell adherence. Lymphocytes (effector cells; 100.□ L) isolated by Ficoll-Hypaque separation (as described above) were then added to the target cells to provide an effector/target cell (E:T) ratio of 10:1. After 10 hours of incubation at 37° C., 20. □ l of a substrate containing 5.□ g of 3-(4,5-dimethylthiazol-2-yl)-2,5-diphenyltetrazolium bromide (MTT) was added. The mixture was incubated for 4 hours at 37° C. after which the unmetabolized MTT was removed by aspira-tion. The formazan crystals were dissolved by adding 200 □ L of 95% ethanol. Optical density was measured at 570 nm using a microplate reader. The percentage of NK cell-specific lysis was calculated as follows:

Specific Cytotoxicity(%)=100×{1−[(OD of target cells and effector cells−OD of effector cells)/(OD of target cells)]}

3. Antibody response to vaccines: The test subjects are given an array (up to 5) of vaccines after at least 12 weeks of probiotic or control feeding. The vaccines may be a mixture of novel and redundant vaccines. Non-limiting examples of vaccine arrays that may be used include mixtures of vaccines prepared by Fort Dodge Animal Health. Non-limiting examples of vaccines suit-able for use herein include Canine distemper, adenovi-rus, coronavirus, parainfluenza, and parvovirus. The test subject's vaccine history will determine the vaccines to be used. The specific antibodies to the vaccines given are measured in blood for 3 weeks and the length and strength of response in control and probiotic feeding groups compared.

4. Delayed-type hypersensitivity: An in vivo, non-invasive method of assessing immune system status. This test comprises an intradermal injection of the polyclonal mitogen Phytohemmaglutinin (PHA) in combination with sheep red blood cells a multivalent vaccine, hista-mine (100 μL of 0.0275 g/L Histamine Phosphate; Greer, Lenoir, N.C.), or PBS (100 μL of Phosphate Buff-ered Saline, 8.5 g/L; Sigma). The immune response to the antigen is recorded as skinfold thickness using cali-pers at time intervals of 0, 24, 48 and 72 hours post-injection. An increase in skinfold thickness is indicative of a greater hypersensitivity response that should be decreased by treatment with the bacteria of the present invention.

Additional methods for determining the effect of the *Bifi-dobacterium* bacteria of the present invention are described in U.S. Pat. Nos. 6,133,323 and 6,310,090.

Furthermore, ameliorating the effects of age may be deter-mined using dual x-ray absorptometry or CT scan for mea-suring body composition, including body fat mass, fat-free mass and bone mineral content. Similarly, this method may be used to determine anatomy changes such as weight loss or bone density in subjects following infection.

The *Bifidobacterium bacteria* of the present invention may also be used in a method for reducing stress levels in com-panion animals. Concentrations of blood stress hormones including epinephrine, norepinephrine, dopamine, cortisol and C-reactive protein may be measured to determine stress levels and their reduction or maintenance. These hormones are recognized biomarkers of stress and can be readily mea-sured using techniques known to those skilled in the art.

Further still, maintenance or improvement of the health of the skin and/or coat system of companion animals, including atopic disease of the skin, may be measured using skin and coat assessments conducted by two trained individuals. Examples of criteria examined during such assessments include:

a) Shedding index: A shedding index is assigned to each test subject by collecting hair produced during a stan-dardized brushing session. The hair is retained and weighed, and control and test subjects compared.

b) Subjective skin/coat evaluations: Trained panelists sub-jectively evaluate skin and coat condition by assessing shedding, dander, shine, uniformity, softness and den-sity.

c) Skin functional assessment: The barrier function of the skin may be assessed by wiping the skin surface with an acetone-soaked gauze. This technique effectively dis-rupts the skin barrier by removing single cell layers and associated lipid fractions of the stratum corneum. Bar-rier disruption is quantified by measuring the increase in transepidermal water loss (TEWL) and the degree of redness of the insulted site using methods known to those skilled in the art. Redness (erythema) scores are obtained using the previously described camera and lighting system. TEWL readings and redness scores are obtained immediately before and after disruption, and at five and 24-hour endpoints to assess the protective and healing properties of skin.

The treatment or prevention of gastrointestinal infection, including diarrhoea, in companion animals may be measured using stool scores. Stools scores may be recorded daily according to the following guidelines and control and test groups compared before and after feeding with the bacteria according to the present invention.

Score: 5 Extremely Dry

This stool is hard and does not stick to surfaces. Stool will roll when pushed. No indentations are made when stool is picked up. Stool is often defecated in groups of individual stools instead of one complete unit. The stool maintains original shape after collection.

Score: 4 Firm (Ideal Stool)

This stool is firm, well shaped, and cylindrical. This stool does not break apart easily when picked up. This stool may leave residue on surfaces and gloves. This stool is often defecated as one unit. The stool maintains original shape after collection.

Score: 3 Soft, with Shape

This stool is soft, however there are definite shapes. This stool will break apart easily and will definitely leave residue on surfaces and gloves. The stool often loses original shape after collection. This stool is often present with another score but can comprise whole stool sample.

Score: 2 Soft, without Shape

This stool is soft and will have no cylindrical shape. The shape often associated with a "2" is a "cow patty" shape. This stool will lose the original shape when collected and will definitely leave residue on surfaces and gloves. This stool score is often present with another score but can comprise the whole stool sample. This stool sample may spread over an area of several inches.

Score: 1 Liquid

This stool score will always resemble liquid and there may or may not be particulate matter present. This stool will often be defecated in groups of piles instead of one complete unit. Mucous is often present with this stool sample. This stool sample is very difficult to collect and residue is always left on surfaces and gloves. This stool sample may spread over an area of several inches.

In addition, other observations are also recorded, including: blood in stool; foreign object in stool; or mucous in stool.

Furthermore, the treatment of gastrointestinal infection in companion animals may comprise improving microbial ecology of companion animals. Improving the microbial ecology of companion animals preferably comprises reducing the levels of pathogenic bacteria in the faeces of companion animals. The levels of pathogenic bacteria present in the faeces of companion animals may be enumerated using the standard plate count method known to those skilled in the art. More preferably, the pathogenic bacteria are selected from the group consisting of *Clostridia, Escherichia, Salmonella*, bacteriodes and mixtures thereof. Non-limiting examples of suitable strains of pathogenic bacteria include *C. perfringens, C. difficile, Eschericia coli, Salmonella typhimurium* and mixtures thereof.

The method of use of the bacteria of the present invention may also include the treatment, either prophylactic or therapeutic of the urinary tract of mammals, preferably companion animals. Non-limiting examples of urinary tract treatment include treatment or prevention of urinary tract infections, treatment or prevention of kidney disease, including kidney stones, treatment or prevention of bladder infections and the like. Without being bound by theory, it is believed that the *Bifidobacteria* of the present invention are useful in preventing these ailments as a result of their ability to degrade oxalic acid, as demonstrated in vitro. Oxalic acid is a by-product of urinary metabolism that can form insoluble precipitates that result in kidney, bladder and other urinary tract infections. By degrading oxalic acid, and therefore potentially preventing its precipitation and build up in the urinary tract, the bacteria of the present invention may treat and prevent infections and other ailments of the urinary tract. Oxalic acid degradation may be measured in vitro using the Oxalic acid test kit cat #755699 commercially available from Boehringer Mannheim/R-Biopharm.

The *Bifidobacteria globosum* of the present invention may be used in a method for improving or maintaining the health of companion animals comprising improving fiber digestion. Improving fiber digestion is desirable as it promotes the growth of said probiotic bacteria, as well as beneficial endogenous microflora, which aid in the suppression of some potentially pathogenic bacteria. In addition, a decrease in the amount of toxic metabolites and detrimental enzymes that result from colonic fermentation has been documented in humans (Tomomatsu, H. "Health effects of oligosaccharides", (1994) Food Technol, 48, 61-65). Fiber digestion may be determined using the method described in Vickers et al. (2001), "Comparison of fermentation of selected fructooligosaccharides and other rfiber substrates by canine colonic microflora", Am. J. Vet. Res. 61 (4), 609-615, with the exception that instead of inoculating using diluted fecal samples each experiment used pure cultures of the bacterial strains of interest.

The method of use of the *Bifidobacterium globosum* bacteria of the present invention typically involves oral consumption by the animal. Oral consumption may take place as part of the normal dietary intake, or as a supplement thereto. The oral consumption typically occurs at least once a month, preferably at least once a week, more preferably at least once per day. The *Bifidobacterium globosum* bacteria of the present invention may be given to the companion animal in a therapeutically effective amount to maintain or improve the health of the animal, preferably a companion animal. As used herein, the term "therapeutically effective amount" with reference to the lactic acid bacteria, means that amount of the bacteria sufficient to provide the desired effect or benefit to a host animal in need of treatment, yet low enough to avoid adverse effects such as toxicity, irritation, or allergic response, commensurate with a reasonable benefit/risk ratio when used in the manner of the present invention. The specific "therapeutically effective amount" will vary with such factors as the particular condition being treated, the physical condition of the user, the duration of the treatment, the nature of concurrent therapy (if any), the specific dosage form to be used, the carrier employed, the solubility of the dose form, and the particular dosing regimen.

Preferably, the lactic acid bacteria are given to the companion animal at a dose of from 1.0E+04 to 1.0E+14 CFU per day, more preferably from 1.0E+06 to 1.0E+12 CFU per day. The composition preferably may contain at least 0.001% of from 1.0E+04 to 1.0E+12 CFU/g of the *Bifidobacterium globosum* obtainable by isolation from resected and washed canine GI tract. The *Bifidobacterium globosum* bacteria can be given to the animal in either viable form, or as killed cells, or distillates, isolates or other fractions of the fermentation products of the lactic acid bacteria of the present invention, or any mixture thereof.

Preferably, the *Bifidobacterium globosum* bacteria, or a purified or isolated fraction thereof, are used to prepare a composition intended to maintain or improve the health of an animal. As indicated above, the composition may be part of the normal dietary intake, or a supplement. Where the composition comprises part of the normal dietary intake, the composition may be in the form of a dried animal food such as biscuits or kibbles, a processed grain feed, a wet animal food, yogurts, gravies, chews, treats and the like.

Such compositions may comprise further components. Other components are beneficial for inclusion in the compositions used herein, but are optional for purposes of the invention. For example, food compositions are preferably nutritionally balanced. In one embodiment, the food compositions may comprise, on a dry matter basis, from about 20% to about 50% crude protein, preferably from about 22% to about 40% crude protein, by weight of the food composition. The crude protein material may comprise any material having a protein content of at least about 15% by weight, non-limiting examples of which include vegetable proteins such as soybean, cotton seed, and peanut, animal proteins such as casein, albumin, and meat tissue. Non-limiting examples of meat tissue useful herein include fresh meat, and dried or rendered meals such as fish meal, poultry meal, meat meal, bone meal and the like. Other types of suitable crude protein sources include wheat gluten or corn gluten, and proteins extracted from microbial sources such as yeast.

Furthermore, the food compositions may comprise, on a dry matter basis, from about 5% to about 35% fat, preferably from about 10% to about 30% fat, by weight of the food composition. Further still, food compositions comprising the lactic acid bacteria of the present invention may also comprise from about 4% to about 25% total dietary fiber. The compositions may also comprise a multiple starch source as described in WO99/51108.

The compositions of the present invention may further comprise a source of carbohydrate. Grains or cereals such as rice, corn, milo, sorghum, barley, alfalfa, wheat, and the like are illustrative sources. In addition, the compositions may also contain other materials such as dried whey and other dairy by products.

The compositions comprising the bacteria of the present invention may also comprise a prebiotic. "Prebiotic" includes substances or compounds that are fermented by the intestinal flora of the pet and hence promote the growth or development of lactic acid bacteria in the gastro-intestinal tract of the pet at the expense of pathogenic bacteria. The result of this fermentation is a release of fatty acids, in particular short-chain fatty acids in the colon. This has the effect of reducing the pH value in the colon. Non-limiting examples of suitable prebiotics include oligosaccharides, such as inulin and its hydrolysis products commonly known as fructooligosaccharides, galacto-oligosaccharides, xylo-oligosaccharides or oligo derivatives of starch. The prebiotics may be provided in any suitable form. For example, the prebiotic may be provided in the form of plant material which contains the fiber. Suitable plant materials include asparagus, artichokes, onions, wheat or chicory, or residues of these plant materials. Alternatively, the prebiotic fiber may be provided as an inulin extract, for example extracts from chicory are suitable. Suitable inulin extracts may be obtained from Orafti SA of Tirlemont 3300, Belgium under the trade mark "Raftiline". For example, the inulin may be provided in the form of Raftiline (g) ST which is a fine white powder which contains about 90 to about 94% by weight of inulin, up to about 4% by weight of glucose and fructose, and about 4 to 9% by weight of sucrose. Alternatively, the fiber may be in the form of a fructooligosaccharide such as obtained from Orafti SA of Tirlemont 3300, Belgium under the trade mark "Raftilose". For example, the inulin may be provided in the form of Raftilose (g) P95. Otherwise, the fructooligosaccharides may be obtained by hydrolyzing inulin, by enzymatic methods, or by using micro-organisms.

For dried pet foods a suitable process is extrusion cooking, although baking and other suitable processes may be used. When extrusion cooked, the dried pet food is usually provided in the form of a kibble. If a prebiotic is used, the prebiotic may be admixed with the other ingredients of the dried pet food prior to processing. A suitable process is described in European patent application No 0850569. If a probiotic micro-organism is used, the organism is best coated onto or filled into the dried pet food. A suitable process is described in European patent publication Number EP 0 862 863.

For wet foods, the processes described in U.S. Pat. Nos. 4,781,939 and 5,132,137 may be used to produce simulated meat products. Other procedures for producing chunk type products may also be used; for example cooking in a steam oven. Alternatively, loaf type products may be produced by emulsifying a suitable meat material to produce a meat emulsion, adding a suitable gelling agent, and heating the meat emulsion prior to filling into cans or other containers. Typical wet food compositions may comprise from about 5% to about 15% protein, from about 1% to about 10% fat, and from about 1% to about 7% fiber. Non-limiting ingredients that may be used in wet food compositions include chicken, turkey, beef, whitefish, chicken broth, turkey broth, beef broth, chicken liver, brewers rice, corn grits, fish meal, egg, beet pulp, chloride, flax meal, lamb, beef by-products, chicken by-products and mixtures thereof.

In another embodiment, supplement compositions such as biscuits, chews, and other treats may comprise, on a dry matter basis, from about 20% to about 60% protein, or from about 22% to about 40% protein, by weight of the supplement composition. As another example, the supplement compositions may comprise, on a dry matter basis, from about 5% to about 35% fat, or from about 10% to about 30% fat, by weight of the supplement composition. Food and supplement compositions intended for use by canines or felines are commonly known in the art.

The pet foods may contain other active agents such as long chain fatty acids and zinc. Suitable long chain fatty acids include alpha-linoleic acid, gamma linolenic acid, linoleic acid, eicosapentanoic acid, and docosahexanoic acid. Fish oils are a suitable source of eicosapentanoic acids and docosahexanoic acid.

Borage oil, blackcurrent seed oil and evening primrose oil are suitable sources of gamma linolenic acid. Safflower oils, sunflower oils, corn oils and soy bean oils are suitable sources of linoleic acid. These oils may also be used in the coating substrates referred to above. Zinc may be provided in various suitable forms, for example as zinc sulfate or zinc oxide. Further, many ingredients commonly used in pet foods are sources of fatty acids and zinc. It has been observed that the combination of chicory, as a source of prebiotic, with a linoleic-acid rich oil, such as soy bean oil, provides unexpected benefits, suggestive of a synergistic effect.

Where the composition is in the form of a gravy, the composition preferably comprises at least 10% of a broth, or stock, non-limiting examples of which include vegetable beef, chicken or ham stock. Typical gravy compositions may comprise from about 0.5% to about 5% crude protein, from about 2% to about 5% crude fat, and from about 1% to about 5% fiber.

Further non-limiting examples of supplements suitable for use herein include powders, oil suspensions, milk-based suspensions cheeses, and pills or capsules. Where the composition is in the form of a pill, suitable binding agents are required to maintain the pill in a solid, pressed form. Non-limiting examples of suitable binding agents include the natural gums such as xanthan gum, pectins, lecithins, alginates and others known to those skilled in the art. Where the composition is in the form of a capsule, the composition is preferably encapsulated using technologies known to those skilled in the art. Non-limiting examples of suitable encapsulation materials include polyvinyl alcohol (PVA), polyvinylpyrrolidone (PVP), alginates, and gelatin. Yogurt-based compositions may comprise from about 1% to about 5% protein, from about 10% to about 20% carbohydrate, from about 1% to about 5% fiber, from about 1% to about 5% fat and from about 50% to about 90% liquid carrier such as milk.

EXAMPLES

The following examples are provided to illustrate the invention and are not intended to limit the scope thereof in any manner.

Example 1

Isolation of *Bifidobacterium globosum* Bacteria from Canine GI Tracts

Canine intestinal samples were obtained from healthy dogs presenting at the local veterinarians for owner initiated and approved euthanasia. All animals were healthy and disease-free. The colon, mid-colon, caecum and ileum of each dog were dissected in order to expose the mucosa.

Supernatants were removed following agitation of the mucosal tissue (vortexed for 1 minute) and following mechanical homogenisation of the tissue. Each supernatant was plated on Reinforced Clostridia Agar (RCA) or MRS plus 0.05% cysteine plus mupirocin. These were incubated anaerobically, using the Anerocult GasPak system, for 24 hours at 37° C. Isolated colonies from the plates were re-streaked onto either MRS or RCA and again grown anaerobically under the same conditions. Isolated colonies were re-streaked a further 4 times in order to purify a single strain. Colony morphology and microscopic appearance were assessed. Suitable isolates were tested for Gram reaction and catalase activity. Identification of gram positive, catalase negative rods was performed using API testing (API 50CHL, BioMerieux). Harvested cells were washed twice with 0.05M phosphate buffer (pH 6.5) and cysteine-HCl (500 mg/l) followed by sonication. Centrifugation removed cellular debris. Supernatants were incubated with NaF (6 mg/ml) and Na iodoacetate (10 mg/ml) for 30 minutes at 37° C. The reaction was stopped by incubation with hydroxylamine HCl (pH6.5) for 10 minutes at room temperature. Colour development was monitored following the addition of HCl (4M), $FeCl_3.6H_2O$ (5% (w/v) in 0.1M HCl) and fructose-6-phosphate (Na salt). Formation of acetyl phosphate from fructose-6-phosphate was evidenced by the reddish colour formed by the ferric chelate of its hydroxymate.

Fifty-eight (58) lactic acid bacterial strains were isolated from resected and washed canine GI tract, of which six were found to be of the genus *Bifidobacterium*, and one of the strain *B. globosum*.

Example 2

Screening for Anti-Microbial Activity

The isolated *Bifidobacterium globosum* bacterial strains were incubated anaerobically in TPY broth. 2 µl of each culture were spotted onto TPY agar plates and incubated anaerobically overnight. *Salmonella typhimurium, Listeria monocytogenes, Listeria innocua* and *Escherichia coli* 0157H45 were pre-grown overnight and 100 µl inoculated into molten agar (1% v/v). This indicator culture was poured onto the surface of the inoculated MRS or TPY plates. Following overnight incubation, zones of inhibition around the probiotic colony were measured. All experiments were performed in duplicate on three separate occasions. In addition, incorporating the buffer 2% betaglycerophosphate into the agar enabled assessment of the contribution of acid production to the observed pathogen inhibition in vitro.

The data presented in FIGS. 1, 2, 3 and 4 clearly demonstrate that the *Bifidobacterium globosum* bacteria strains of the present invention obtainable by isolation from resected and washed canine GI tract have anti-microbial activity in vitro, indicative of potential probiotic activity.

Example 3

In Vitro Measures of Survival and Colonisation pH Tolerance

Bacterial cells were harvested from overnight cultures, washed twice in phosphate buffer (pH 6.5) and resuspended in TPY broth adjusted with 1M HCl to pH 2.5. The cells were incubated anaerobically at 37° C. and their survival measured at intervals of 0, 30, 60, 120, 240 and 360 minutes using the plate count method known to those skilled in the art.

Figure 5:
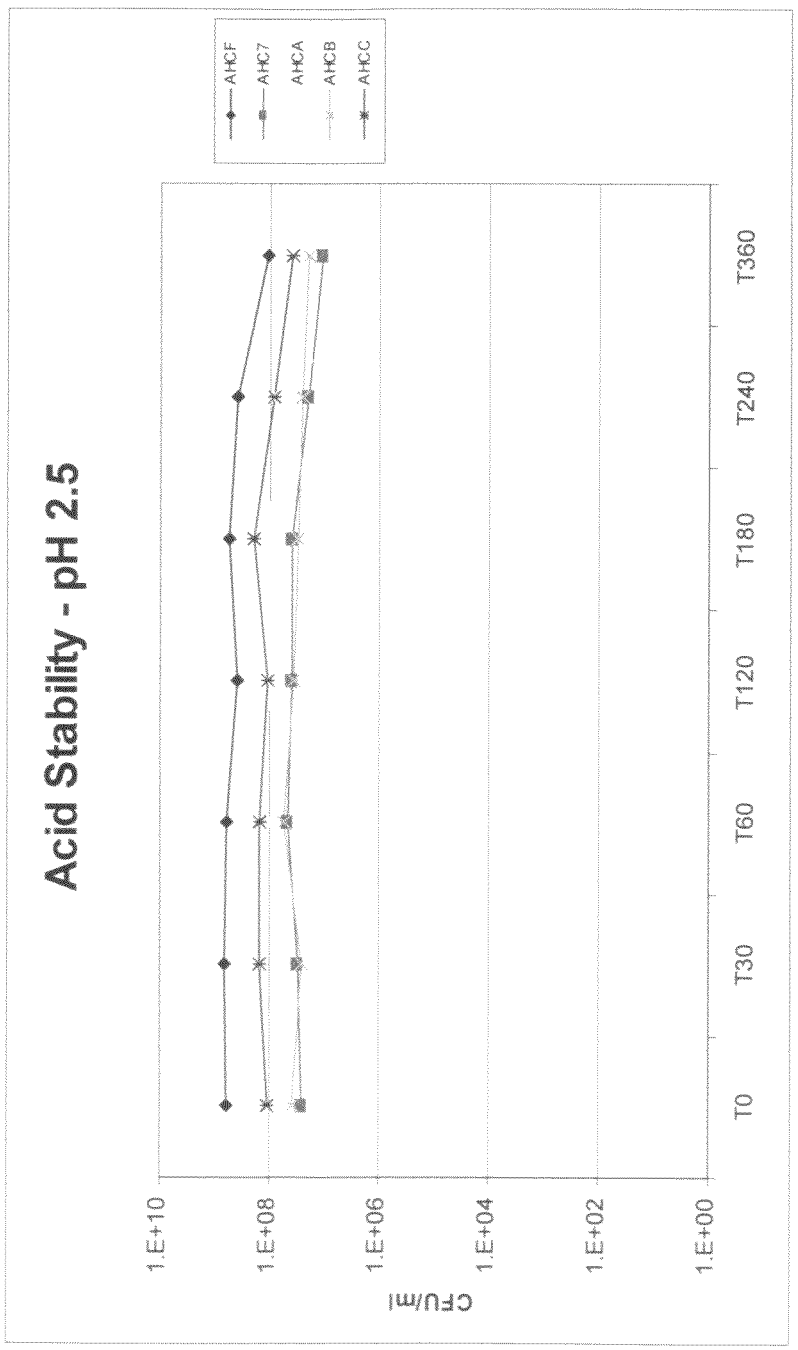
FIG. 5 demonstrates the in vitro acid stability of the *Bifidobacterium globosum* bacteria of the present invention according to methodology set out in example 3.

FIG. 5 clearly demonstrates that five strains were resistant to pH 2.5 over 1 hour. Table 2 summarises this data per strain.

TABLE 2

| Strain designation | Starting Conc. | Conc. After 1 hour | Viability (%) |
|---|---|---|---|
| AHC A | 1.50E+08 | 1.20E+08 | 80 |
| AHC B | 4.00E+07 | 5.50E+07 | 137 |
| AHC C | 1.10E+08 | 1.50E+08 | 136 |
| AHC F | 6.00E+08 | 6.00E+08 | 100 |
| AHC 7 | 2.50E+07 | 4.50E+07 | 180 |

Bile Resistance

The bacterial strains were streaked onto TPY agar supplemented with porcine bile (Sigma) at 0.5%, 1% and 5% (w/v). Plates were incubated at 37° C. under anaerobic conditions and the growth recorded after 24 hours. Growth was compared with control plates by an experienced observer, and the growth of colonies described as:

Negative (0)— no growth;

+ (1)—Hazy translucent growth (<33% control-plates with 0% bile);

++ (2)—Definite growth but not as good as controls (>33% but <66%);

+++ (3)—Growth equivalent to controls (>66%).

Once the growth of the colonies in the presence of bile salts is compared with the controls, the growth descriptors are given numerical values of 0, 1, 2 or 3 (−; +; ++, +++ respectively), and then expressed as a percentage, where 3 represents 100%.

Figure 6:
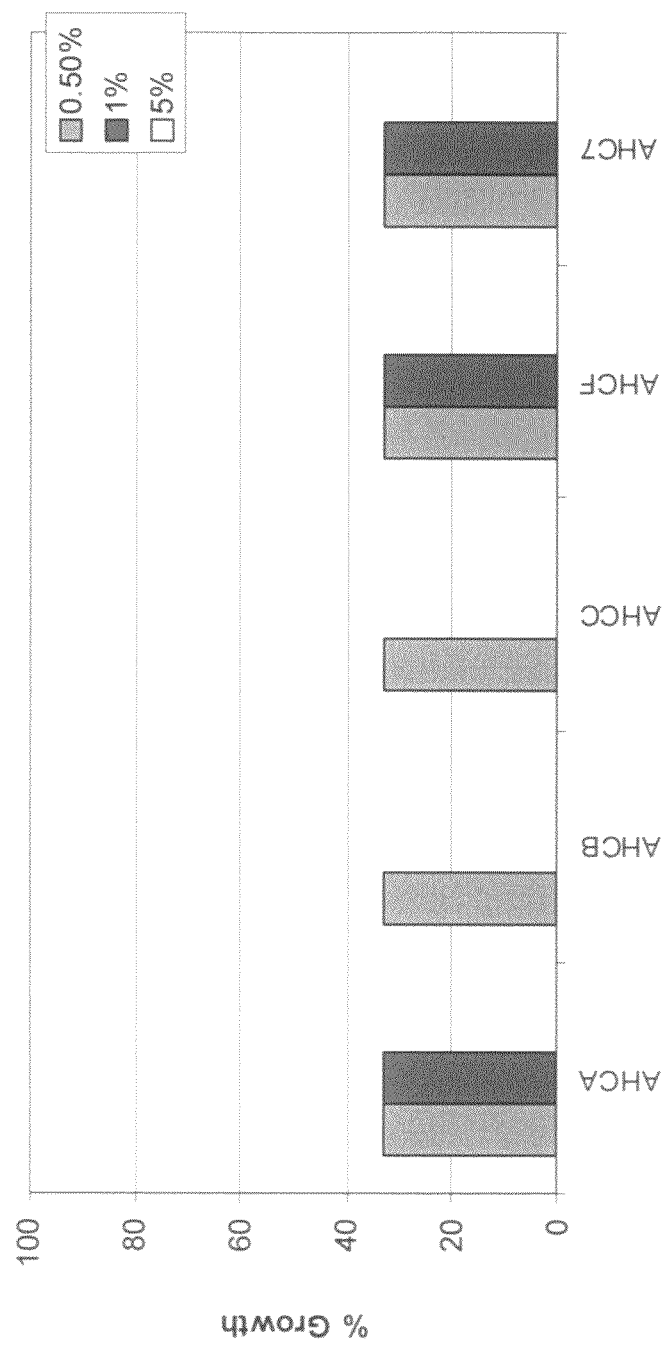
FIG. 6 demonstrates the growth characteristics of the *Bifidobacterium globosum* bacteria of the present invention in the presence of 0.5%, 1% and 5% porcine bile salts.

FIG. 6 demonstrates that the *Bifidobacterium* bacteria of the present invention clearly demonstrate a resistance to bile salts, being able to grow and form colonies at a level of at least 33% when exposed to 0.5% bile salts.

Gut Epithelial Cell Adhesion

The human epithelial cell line, HT-29, was used to assess the adhesion properties of selected strains. Epithelial cells were routinely cultured as a monolayer in 75 $cm^2$ tissue culture flasks at 37° C. in a humidified atmosphere containing 5% $CO_2$ in Dulbecco's Minimal Essential Media (DMEM) containing 10% foetal calf serum (FCS), pen/strep, glutamine and fungizone. For experimental purposes, the epithelial cells were seeded at a concentration of $5\times10^5$ cells/ml (3 mls total volume) per well in 6 well culture plates (Sarstedt). Following incubation for 7 days, to allow differentiation, the epithelial monolayers were washed with antibiotic-free medium containing 10% FCS. Bacterial suspensions plus/in antibiotic-free DMEM were added to each well and the cells incubated for 90 minutes at 37° C. Following incubation, the monolayers were washed three times with PBS. The epithelial cells were lysed in deionised $H_2O$ and the number of adherent bacteria enumerated using the plate count method known to those skilled in the art. Adhesion was expressed as a percentage of the number of bacteria initially plated.

Figure 7:
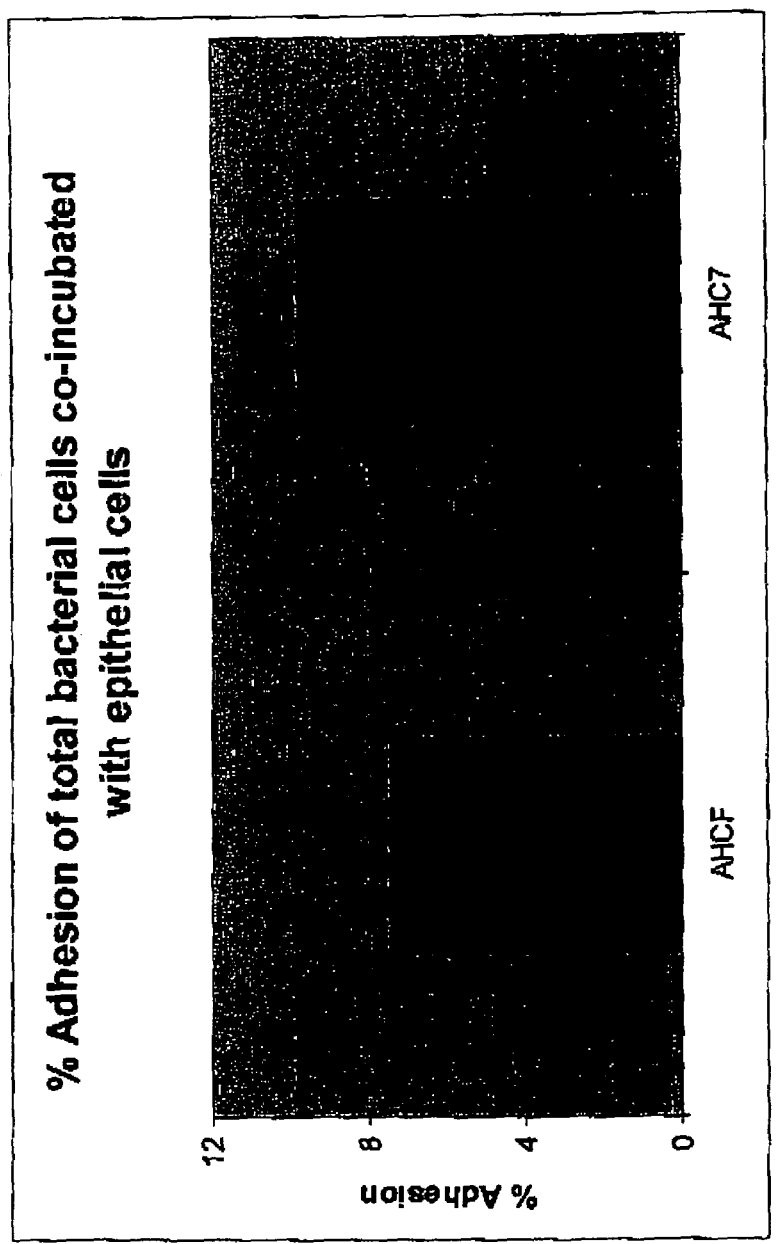
FIG. 7 demonstrates the in vitro ability of the *Bifidobacterium globosum* bacteria of the present invention to adhere to HT-29 gut epithelial cells.

As can be seen from FIG. 7, the *Bifidobacterium globosum* strain deposited with the NCIMB under deposition numbers NCIMB 41198 adhere to HT-29 gut epithelial cells at levels of at least 4%.

Example 4

16s-23s Intergenic Polynucleotide Sequencing

*Bifidobacterium globosum* colonies were picked from an Agar plate and resuspended in 1×PCR buffer, heated at 96° C. for 5 minutes, frozen at −70° C. for 5-10 minutes, thawed and an aliquot was added to a PCR eppendorf tube. PCR was performed using the intergenic spacer (IGS) primers, IGS L: 5'-GCTGGATCACCTCCTTTC-3' and IGS R: 5'-CTGGT-GCCAAGGCATCCA-3'. The cycling conditions were 96° C. for 1 min (1 cycle), 94° C. for 30 sec, 53° C. for 30 sec, 72° C. for 30 sec (28 cycles). The PCR reaction contained 5 µl of DNA, PCR buffer (Bioline, UK), 0.2 mM dNTPs (Roche, UK), 0.4☐ M IGS L and R primer (150 ng/50 µl) (MWG Biotech, Germany) and Bioline Taq polymerase (0.6 units). The PCR reactions were performed on a Hybaid thermocycler. The PCR products (8 µl) were ran alongside a molecular weight marker (ΦX174 Hae III, Promega) on a 2% agarose EtBr stained gel in TAE, to determine their IGS profile. Using the same primers as above, the intergenic spacer (IGS) DNA was sequenced for the 2 canine *Bifidobacterium globosum* strains using methods known to those skilled in the art.

Following sequencing, the obtained sequences for the four deposited strains were compared with the on-line sequence database "BLAST", available at http://www.ncbi.nlm.nih.gov/BLAST/ for homology with other deposited bacterial 16s-23s sequences. The closest match for AHCF was *Bifidobacterium pseudolongum* ATCC 25526, having homology scores of 92%. However, the several differences exist between these strains and between each other.

Example 5

Example Compositions

Examples 1 to 4 are examples of dried kibble compositions comprising the probiotic *Bifidobacterium globosum* of the present invention.

| Ingredient | Percentage on a weight Basis | | | |
|---|---|---|---|---|
| | Ex. 1 | Ex. 2 | Ex. 3 | Ex. 4 |
| Cereal grains | To 100 | To 100 | To 100 | To 100 |
| Poultry by-product meal | 43.5 | 40 | 45 | 35 |
| Poultry fat | 1.28 | 1.02 | 1.16 | 1.35 |
| Egg product | 2.4 | 2.1 | 2.5 | 2.2 |
| Chicken liver meal | 1.0 | 1.0 | 1.0 | 1.0 |
| Brewer's dried yeast | 1.0 | 1.0 | 1.0 | 1.0 |
| Monosodium phosphate | 1.0 | 1.0 | 1.0 | 1.0 |
| Calcium carbonate | 0.8 | 0.8 | 0.8 | 0.8 |
| Potassium chloride | 0.6 | 0.6 | 0.6 | 0.6 |
| Vitamins | 0.4 | 0.4 | 0.4 | 0.4 |
| Choline chloride | 0.3 | 0.3 | 0.3 | 0.3 |
| Minerals | 0.3 | 0.3 | 0.3 | 0.3 |
| DL-Methionine | 0.1 | 0.1 | 0.1 | 0.1 |
| Sodium Chloride | 0.03 | 0.03 | 0.03 | 0.03 |
| Probiotic (1 × $10^{10}$ cfu/g NCIMB 41198 in sunflower oil) | 1 | 0.5 | 0.1 | 0.6 |

Examples 5 to 7 are examples of wet pet food compositions comprising the probiotic *Bifidobacterium globosum* of the present invention.

| Ingredient | Percentage on a weight Basis | | |
|---|---|---|---|
| | Ex. 5 | Ex. 6 | Ex. 7 |
| Water | To 38 | To 47 | To 50 |
| Poultry Liver | To 25 | To 20 | To 15 |
| Poultry Products | 25 | 20 | 20 |
| Brewers Rice | 5 | 7 | 10 |
| Egg Product | 3 | 2.5 | 1.5 |
| Poultry Fat | 2.9 | 3.0 | 3.2 |
| Chicken Stock | 0.6 | 0.7 | 0.9 |
| Taurine | 0.1 | 0.1 | 0.1 |
| Vitamins | 0.05 | 0.1 | 0.1 |
| Minerals | 0.05 | 0.1 | 0.1 |
| Probiotic (1 × $10^{10}$ cfu/g NCIMB 41198) | 4 | 5 | 6 |

Examples 8 to 10 are examples of yogurt supplement compositions comprising the probiotic *Bifidobacterium globosum* of the present invention.

| Ingredient | Percentage on a weight Basis | | |
|---|---|---|---|
| | Ex. 8 | Ex. 9 | Ex. 10 |
| Milk | 82.75 | 81.9 | 82.7 |
| Sugar | 12 | 12 | 10 |
| Modified Starch | 1.0 | 0.8 | 0.8 |
| Prebiotic | 0.25 | 0.3 | 0.5 |
| Probiotic (1 × $10^{10}$ cfu/g NCIMB 41198) | 4 | 5 | 6 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating diarrhea in a canine comprising orally administering to the canine a composition comprising an amount of the strain *Bifidobacterium globosum* AHCF, NCIMB 41198, effective to treat diarrhea in the canine.

2. The method according to claim 1 wherein the composition is administered as part of a normal dietary intake.

3. The method of claim 1 wherein the composition is administered as part of a supplement.

4. The method of claim 1 wherein the composition is administered at least once per month.

5. The method of claim 1 wherein the composition comprises from about $10^4$ CFU to about $10^{12}$ CFU of the strain.

6. The method of claim 1 wherein the strain is in viable form or in the form of killed cells.

7. The method of claim 1, wherein the strain is obtainable from washed GI tract of a canine.

* * * * *

SEQUENCE LISTING

<160> NUMBER OF SEQ ID NOS: 3

<210> SEQ ID NO 1
<211> LENGTH: 556
<212> TYPE: DNA
<213> ORGANISM: Bifidobacteria Globosum NCIMB 41198
<220> FEATURE:
<221> NAME/KEY: misc_feature
<222> LOCATION: (460)..(460)
<223> OTHER INFORMATION: n is c, g, a or t.
<220> FEATURE:
<221> NAME/KEY: misc_feature
<222> LOCATION: (549)..(549)
<223> OTHER INFORMATION: n is c, g, a or t.

<400> SEQUENCE: 1

```
acgatttgtg ggcgcacggt ggtgcgccga tatggggatg cttccttttc ctggccgtct        60
ggccgggtgg cgtcccttgc tggctgggaa aagggtcaag gcgcctgcgc ccgttgtggt       120
gtgggtggtg gtggtgtggt gcatgctgtt gggttcccgg accgccaggc cccttgtcgg       180
gggtggtgtt ccgttcccgc cgtcctggcc gtgcccctgt gtggggtggg tgcctggggt       240
ggtgtggtgt ggtggtttga gaactggaga gtggacgcga gcatgaacgg tgtgccctgt       300
ggggtgtgcc gggtgtgttc gtactgttga ttttgtcgaa ccgttccatc cccgcctttt       360
gggttggggg tgttggattg tgttcgcgag tgttttggta gagccgtcca cgcccgtgtg       420
ggtgtgggtg gtgtttagat gatctgatta gttgtcgtan ggtgttccag tgcaagtggc       480
atgggcccgt ggcccccttt tgcggggttg gtgggtttgt tgccatgggc gtatggtgga       540
atgcctgtnc accacg                                                      556
```

<210> SEQ ID NO 2
<211> LENGTH: 18
<212> TYPE: DNA
<213> ORGANISM: Artificial
<220> FEATURE:
<223> OTHER INFORMATION: Chemically synthesized nucleotide sequence

<400> SEQUENCE: 2
gctggatcac ctcctttc        18

<210> SEQ ID NO 3
<211> LENGTH: 18
<212> TYPE: DNA
<213> ORGANISM: Artificial
<220> FEATURE:
<223> OTHER INFORMATION: Chemically synthesized nucleotide sequence

<400> SEQUENCE: 3
ctggtgccaa ggcatcca        18